United States Patent [19]

Nelson et al.

[11] Patent Number: 4,727,069

[45] Date of Patent: Feb. 23, 1988

[54] HETEROCYCLIC AMINOALKYL ESTERS OF MYCOPHENOLIC ACID, DERIVATIVES THEREOF AND PHARMACEUTICAL COMPOSITIONS

[75] Inventors: Peter H. Nelson, Los Altos; Chee-Liang L. Gu, Sunnyvale; Anthony C. Allison, Belmont; Elsie M. Eugui, Belmont; William A. Lee, Menlo Park, all of Calif.

[73] Assignee: Syntex (U.S.A.) Inc., Palo Alto, Calif.

[21] Appl. No.: 8,909

[22] Filed: Jan. 30, 1987

[51] Int. Cl.$^4$ .................. A61K 31/535; A61K 31/55; C07D 295/14
[52] U.S. Cl. ...................................... 514/211; 514/212; 514/218; 514/222; 514/236; 514/253; 514/320; 514/365; 514/378; 514/385; 514/403; 514/422; 540/544; 540/575; 540/553; 540/596; 544/58.7; 544/153; 544/376; 546/196; 548/146; 548/240; 548/300; 548/356; 548/525

[58] Field of Search ............... 540/544, 575, 553, 596; 544/58.7, 153, 376; 546/196; 548/146, 240, 300, 356, 525; 514/211, 212, 218, 222, 236, 253, 320, 365, 378, 385, 403, 422

[56] References Cited

PUBLICATIONS

"Antitumor Activity of Derivatives of Mycophenolic Acid", Suzuki, et al., J. Antibiotics, 29(3), 275–285, 1975.

"Antitumor and Immunosuppressive Effects of Mycophenolic Acid", Ohsugi et al., Cancer Research, 36, 2923–2927, 1976.

*Primary Examiner*—Robert W. Ramsuer
*Attorney, Agent, or Firm*—David A. Lowin; Tom M. Moran

[57] ABSTRACT

Heterocyclic aminoalkyl esters of mycophenolic acid, and the derivatives and pharmaceutically acceptable salts thereof, are useful as immunosuppressive agents, anti-inflammatory agents, anti-tumor agents, anti-viral agents, and anti-psoriatic agents.

9 Claims, No Drawings

HETEROCYCLIC AMINOALKYL ESTERS OF MYCOPHENOLIC ACID, DERIVATIVES THEREOF AND PHARMACEUTICAL COMPOSITIONS

FIELD OF THE INVENTION

1. Field of the Invention

The present invention relates to pharmaceutical compositions, particularly to aminoalkyl esters of mycophenolic acid and derivatives thereof, and to their use as immunosuppressive and anti-inflammatory agents. For example, they are useful for treating rheumatoid arthritis, in which there is an immunologically driven inflammatory process. Because of their effects on purine metabolism, the pharmaceutical compositions of the present invention also find use as anti-tumor, anti-viral and anti-psoriatic agents.

2. Cross-Reference to Related Applications

This application is related to Ser. No. 008,717, entitled "Morpholinoethylester of Mycophenolic Acid and Derivatives Thereof," filed contemporaneously herewith; to Ser. No. 803,041, filed Nov. 27, 1985; and to Ser. No. 821,633, filed Jan. 23, 1986.

3. Background Information and Related Disclosures

Inflammatory diseases, in particular rheumatoid arthritis, have been treated with a variety of compounds representing several structural classes and biological activities, including, for example, anti-inflammatory agents (corticosteroids, aspirin, derivatives of arylacetic and arylpropionic acids, and oxicams), immunosuppressive agents and regimes (methotrexate, cyclophosphamide, cyclosporin, and total lymphoid irradiation), and long-acting anti-rheumatic drugs (gold salts, and penicillamine and its derivatives). However, no representative of any of these classes of compounds is regarded as ideal.

Mycophenolic acid is a weakly-active antibiotic found in the fermentation broth of *Penicillium brevicompactum*. Some compounds relating to mycophenolic acid, and their uses in the treatment of inflammatory diseases, such as rheumatoid arthritis, are disclosed in the following two prior related applications.

Ser. No. 803,041, filed Nov. 27, 1985, now U.S. Pat. No. 4,686,234 relates to compounds having the general structure of Formula 1:

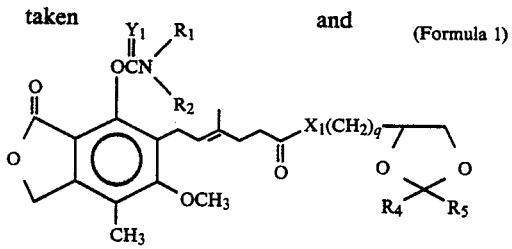

(Formula 1)

and the pharmaceutically acceptable salts thereof, where:

$R_1$ is H or lower alkyl having 1 to 6 carbon atoms;
$R_2$ is H, lower alkyl having 1 to 6 carbon atoms or -phenyl-4-$CO_2R_3$, in which $R_3$ is H, lower alkyl having 1 to 6 carbon atoms or a pharmaceutically acceptable cation;
$R_4$ and $R_5$ are each independently H or lower alkyl having 1 to 6 carbon atoms;
$X_1$ and $Y_1$ are each independently O or S; and
q is an integer of 1-6.

Ser. No. 821,633, filed Jan. 23, 1986, relates to compounds having the general structure of Formula 2:

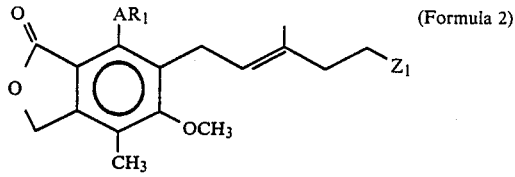

(Formula 2)

and the pharmaceutically acceptable salts thereof, where:

A is oxygen or sulfur;
$R_1$ is selected from the group consisting of:

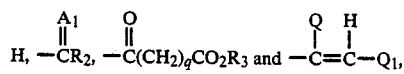

in which:

$A_1$ is oxygen or sulfur;
q is an integer from 0-6;
$R_2$ is alkyl, haloalkyl or $-NR_4R_5$, where:
  $R_4$ and $R_5$ are independently H, alkyl, haloalkyl, cycloalkyl, phenyl optionally monosubstituted with halogen, hydroxy, carboxy, chlorocarbonyl, sulfonylamino, nitro, cyano, phenyl, alkyl, acyl, alkoxycarbonyl, acylamino, dialkylamino or dialkylaminoethoxycarbonyl, phenyl optionally disubstituted with hydroxy, carboxy, nitro or alkyl, or benzyl optionally substituted with dialkylamino;
$R_3$ is H, alkyl or a pharmaceutically acceptable cation;
Q and $Q_1$ are independently H or $-CO_2R_3$; and
$Z_1$ is selected from the group consisting of: IH-tetrazolyl, $-CH_2OH$, $-CHO$, $-CN$, $-C(O)A_2R_6$ and $-C(O)NR_7R_8$, in which:
  $A_2$ is oxygen or sulfur;
  $R_6$ is H, alkyl, alkenyl, cycloalkyl, optionally substituted phenyl, optionally substituted benzyl or a pharmaceutically acceptable cation; and
  $R_7$ and $R_8$ are independently H, alkyl or cycloalkyl, or together $-(CH_2)_2O(CH_2)_2-$, $-(CH_2)_4-$, or $-(CH_2)_5-$;

with the proviso that $R_1$ and $R_6$ cannot both be H if A and $A_2$ are oxygen.

Compounds somewhat structurally similar to the compounds of Formulae 1 and 2 are described in U.S. Pat. Nos. 3,705,894; 3,853,919; 3,868,454; 3,880,995, in Japanese Pat. No. J 57024380, in *J. Antibiot.*, 29(3), 275-85, 286-91 (1976), and in *Cancer Research*, 36(8), 2923-7 (1976). The disclosed compounds are described as having anti-tumor, immunosuppressive, anti-viral, anti-arthritic and/or anti-psoriastic activities.

SUMMARY OF THE INVENTION

One aspect of the present invention concerns the heterocyclic aminoalkyl esters of mycophenolic acid and derivatives thereof, and the pharmaceutically acceptable salts thereof, i.e., the compounds of Formula I:

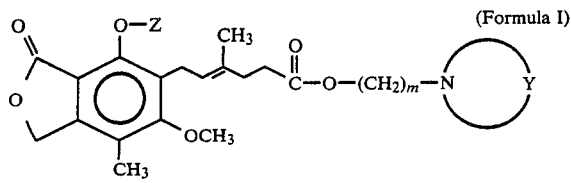 (Formula I)

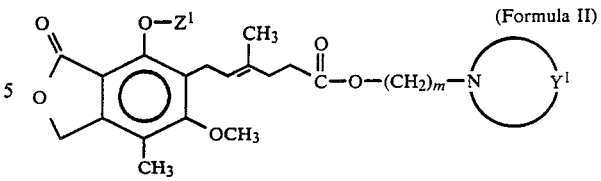 (Formula II)

wherein:
m is an integer from two to four;
Z is selected from Formulae (a) (b) (c) or (d), as follows:
(a)

in which:
$R^1$ is hydrogen, alkyl having seven or more carbon atoms including cycloalkyl such as adamantyl, or —$NR^2R^3$,
where $R^2$ is hydrogen or lower alkyl, and
$R^3$ is hydrogen, lower alkyl, -phenyl-4-$CO_2R^2$ or a pharmaceutically acceptble cation;
(b)

in which:
$R^4$ is hydrogen, alkyl, aryl, or —$NR^2R^3$;
(c)

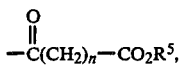

in which:
n is an integer from zero to six, and
$R^5$ is hydrogen, lower alkyl, or a pharmaceutically acceptable cation;
(d)

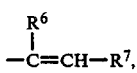

in which:
$R^6$ and $R^7$ are independently hydrogen or —$CO_2R^5$; and
Y is lower alkylene of four to six carbon atoms, or lower alkylene of three to five carbon atoms and one member that is —O—, —S—, or

where $R^8$ is hydrogen or alkyl of one to five carbon atoms.

Another aspect of the present invention concerns the heterocyclic aminoalkyl esters (excluding the morpholinoethyl ester) of mycophenolic acid and certain derivatives of mycophenolic acid, i.e, compounds having the structure of Formula II, which follows:

wherein:
m is an integer from two to four;
$Z_1$ is hydrogen or —$C(O)R^9$,
where $R^9$ is lower alkyl or aryl; and $Y^1$ is lower alkylene of four to six carbon atoms, or lower alkylene of three to five carbon atoms and one member that is —O—, —S—, or

where $R^8$ is hydrogen or alkyl of one to five carbon atoms; and the pharmaceutically acceptable salts thereof;
except that when m is two, $Y^1$ does not include —$(CH_2)_2$—O—$(CH_2)_2$—.

In yet another aspect, the invention relates to a pharmaceutical composition containing a therapeutically effective amount of a compound of Formula I or II admixed with at least one pharmaceutically acceptable excipient.

In still another aspect, the invention relates to a method of treating autoimmune disorders, psoriasis, inflammatory diseases including in particular rheumatoid arthritis, and for treating tumors and viruses in a mammal by administering to a mammal in need of such treatment a therapeutically effective amount of a compound of Formula I or II.

Compounds of Formulae I and II have advantageous pharmacokinetic properties, for example, solubility in the delivery environment (e.g., the stomach), peak plasma concentration, maximum plasma concentration, and improved activity, e.g., anti-inflammatory activity as compared to mycophenolic acid.

DETAILED DESCRIPTION OF THE INVENTION

Definitions and General Parameters

The following definitions are set forth to illustrate and define the meaning and scope of the various terms used to describe the invention herein.

The numbering of the mycophenolic acid is as follows:

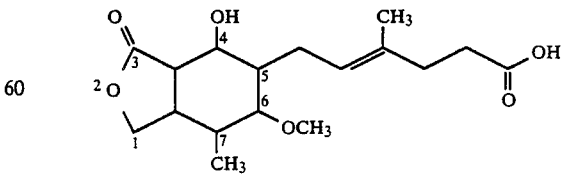

The compounds of the invention will be named using the above-shown numbering system as the morpholinoethyl esters of E-6-(1,3-dihydro-4-hydroxy-6-methoxy-7-methyl-3-oxo-5-isobenzofuranyl)-4-methyl-4-hexenoic acid and its derivatives. The compounds of the present invention are prepared as the E (or Entgegen) position isomer. Some representative compounds are named as follows:

the compound of Formula I where m is 2, Y is —(CH$_2$)$_2$—O—(CH$_2$)$_2$—, Z is —C(O)R$^1$ and wherein R$^1$ is 1-adamantyl, is named "morpholinoethyl E-6-[1,3-dihydro-4-(1-adamantoyloxy)-6-methoxy-7-methyl-3-oxo-5-isobenzofuranyl]-4-methyl-4-hexenoate";

the compound of Formula I where m is 4, Y is —(CH$_2$)$_3$—, Z is —C(O)NR$^2$R$^3$, R$^2$ is 4-carboxyphenyl and R$^3$ is hydrogen, is named "4-(pyrrolidin-1-yl)butyl E-6-{1,3-dihydro-4-[N-(4-carboxyphenyl)carbamoyloxy]-6-methoxy-7-methyl-3-oxo-5-isobenzofuranyl}-4-methyl-4-hexenoate";

the compound of Formula I where m is 2, Y is —(CH$_2$)$_2$—S—(CH$_2$)$_2$—, Z is —C(S)NR$^2$R$^3$, R$^2$ is methyl and R$^3$ is isobutyl, is named "2-(4-thiazin-1-yl)ethyl (E)-6-{1,3-dihydro-4-(N-methyl-N-isobutylthiocarbamoyloxy)-6-methoxy-7-methyl-3-oxo-5-isobenzofuranyl}-4-methyl-4-hexenoate";

the compound of Formula I where m is 2, Y is —(CH$_2$)$_2$—N(CH$_3$)—(CH$_2$)$_2$—, Z is —(O)C(CH$_2$)$_n$—CO$_2$R$^5$, n is 1, and R$^5$ is methyl, is named "2-(4-methylpiperazin-1-yl)ethyl (E)-6-[1,3-dihydro-4-(carbomethoxyethanoyloxy)-6-methoxy-7-methyl-3-oxo-5-isobenzofuranyl]-4-methyl-4-hexenoate";

the compound of Formula I where m is 2, Y is —(CH$_2$)$_2$—O—(CH$_2$)$_2$—, Z is —(O)C(CH$_2$)$_n$—CO$_2$R$^5$, n is 2, and R$^5$ is ethyl, is named "2-(morpholin-1-yl)ethyl (E)-6-[1,3-dihydro-4-(3-carboethoxypropanoyloxy)-6-methoxy-7-methyl-3-oxo-5-isobenzofuranyl]-4-methyl-4-hexenoate";

the compound of Formula I where m is 4, Y is —(CH$_2$)$_2$—N[C—(CH$_3$)$_3$]—(CH$_2$)$_3$—, Z is —(R$_6$)C=CH—R$^7$, R$^6$ is COOH, and R$^7$ is COOH, is named "4-(4-t-butyl-1,4-perhydroazepin-1-yl)butyl (E)-6-[1,3-dihydro-4-(1,2-dicarboxyeth-(E)-enyloxy)-6-methoxy-7-methyl-3-oxo-5-isobenzofuranyl]-4-methyl-4-hexenoate";

the compound of Formula I where m is 3, Y is —(CH$_2$)$_2$—O—(CH$_2$)$_2$—, Z is —(R$_6$)C=CH—R$^7$, R$^6$ is COOMe, and R$^7$ is COOEt, is named "3-(morpholin-1-yl)propyl (E)-6-[1,3-dihydro-4-(2-carboethoxy-1-carbomethoxy-eth-1-(E)-enyloxy)-6-methoxy-7-methyl-3-oxo-5-isobenzofuranyl]-4-methyl-4-hexenoate";

the compound of Formula II where m is 3, Y$^1$ is —(CH$_2$)$_4$—, and Z$^1$ is hydrogen is named "piperazinopropyl E-6-(1,3-dihydro-4-hydroxy-6-methoxy-7-methyl-3-oxo-5-isobenzofuranyl)-4-methyl-4-hexenoate"; and the compound of Formula II where m is 4, Y$^1$ is —O—(CH$_2$)$_5$—, and Z$^1$ is benzoyl is named "4-(perhydro-2-oxazepin-1-yl)butyl E-6-(1,3-dihydro-4-benzoyloxy-6-methoxy-7-methyl-3-oxo-5-isobenzofuranyl)-4-methyl-4-hexenoate".

As used herein, the term "alkyl" refers to a fully saturated monovalent radical containing only carbon and hydrogen, and which may be a cyclic, branched or straight chain radical. This term is further exemplified by radicals such as methyl, ethyl, t-butyl, pentyl, pivalyl, heptyl and adamantyl.

The term "lower alkyl" refers to a monovalent alkyl radical of one to six carbon atoms. This term is further exemplified by such radicals as methyl, ethyl, n-propyl, isopropyl, n-butyl, t-butyl, i-butyl (or 2-methylpropyl), isoamyl, pentyl, and i-pentyl.

The term "alkylene" refers to a fully saturated divalent radical containing only carbon and hydrogen, and which may be a branched or straight chain radical. This term is further exemplified by radicals such as methylene, ethylene, n-propylene, t-butylene, i-pentylene, and n-heptylene.

The term "lower alkylene" refers to a divalent alkyl radical of one to six carbon atoms. This term is further exemplified by such radicals as methylene, ethylene, n-propylene, i-propylene, n-butylene, t-butylene, i-butylene (or 2-methylpropylene), isoamylene, pentylene, and n-hexylene.

The term "aryl" refers to a substituted or unsubstituted monovalent unsaturated aromatic carbocyclic radical having a single ring (e.g., phenyl) or two condensed rings (e.g., naphthyl).

The term "acyl" refers to a radical based on an organic acid, e.g., —C(O)R where R is alkyl or aryl.

As used herein, the term "halo" refers to fluoro, bromo, chloro and iodo.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be found by reference to the examples hereinbelow. However, other equivalent separation or isolation procedures can, of course, also be used.

A "pharmaceutically acceptable salt" may be any salt derived from an inorganic or organic acid or base. The term "pharmaceutically acceptable anion" refers to the anion of such acid addition salts. "Pharmaceutically acceptable cation" refers to the cation of such base addition salts. The salt, the anion, and/or the cation are chosen not to be biologically or otherwise undesirable.

The anions are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluensulfonic acid and the like.

The cations derived from inorganic bases include sodium, potassium, lithium, ammonium, calcium, magnesium and the like. Cations derived from organic bases include those formed from primary, secondary and tertiary amines, such as isopropylamine, diethylamine, trimethylamine, pyridine, cyclohexylamine, ethylene diamine, monoethanolamine, diethanolamine, triethanolamine and the like.

As used herein, the terms "inert organic solvent" or "inert solvent" mean a solvent inert under the conditions of the reaction being described in conjunction therewith (including, for example, benzene, toluene, acetonitrile, tetrahydrofuran, diethyl ether, chloroform, methylene chloride, pyridine and the like).

As used herein, the term "treatment" or "treating" means any treatment of a disease in a mammal, and includes:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

Unless specified to the contrary, the reactions described herein take place at atmospheric pressure over a temperature range from about 10° C. to about 100° C., more preferably from about 10° C. to about 50° C., and most preferably at about room temperature.

Preparation of the Compounds of Formulae I and II

The compounds of Formulae I and II can be prepared according to several synthetic pathways, depending upon the substitution at Z or $Z^1$. Where Z or $Z^1$ is not hydrogen (hereinafter the "4-substituted derivatives"), the phenolic oxygen of mycophenolic acid can be substituted either before or after the esterification of the acid. Where Z or $Z^1$ is hydrogen, the starting material is typically mycophenolic acid, a commercially available compound.

Many of the synthetic routes and/or final synthetic steps for the starting materials of the 4-substituted derivatives are available from the published scientific and patent literature. For example, some such methods are described in U.S. Pat. Nos. 3,705,894, 3,777,020, and 3,868,454, Japanese Kokai Nos. 57/183776, 57/183777, and 48/86860, South African Application No. 68/4959, Great Britain Pat. No. 1261060, Belgian Pat. No. 815330, and West German Pat. No. 2237549, and in related the U.S. application Ser. Nos. 803,041 and 821,633, the relevant portions of which are incorporated herein by reference.

Esterification of Mycophenolic Acids

Many standard esterification procedures may be used, for example, as described in *Synthetic Organic Chemistry* by Wagner and Zook (Wiley, New York) 1956, see pages 479–532. Two presently preferred synthetic routes are described below for conversion of mycophenolic acid and its 4-substituted derivatives into the heterocyclic aminoalkylester compounds of Formulae I and II. The first route involves conversion into an acid halide, followed by condensation with a desired alcohol to form the end product. The second route involves conversion directly into the end product using a carbodiimide reaction.

As an example, a less preferred third route entails starting with an ester of mycophenolic acid (other than the desired heterocyclic aminoalkylester) in an ester exchange reaction, for conversion into the desired end product.

The Acid Halide-Condensation Route

In the first synthetic route, mycophenolic acid or a 4-substituted derivative thereof (i.e., a compound of Formula A, in which $Z^2$ is the same as Z and $Z^1$ in the Summary of the Invention, and M is —OH)

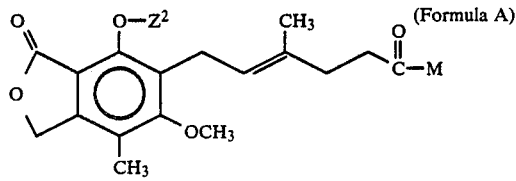

is dissolved or suspended in an inert organic solvent, preferably methylene chloride, and an excess (about 10 molar equivalents to 1) of a halogenating agent (e.g., thionyl chloride) is added, optionally together with a small amount of dimethylformamide. The reaction mixture is stirred for about 1–8 hours, preferably about 4 hours, to yield the corresponding acid halide.

The acid halide is dissolved in an inert solvent, as described above, and reacted by a condensation reaction with a cooled solution (e.g., maintained at about 4° C.) of a heterocyclic aminoalkanol, such as the compounds of Formula B

(in which m and Y are as previously defined in the Summary of the Invention and include, for example, 1-piperidineethanol, morpholinoethanol [also named 4-(2-hydroxyethyl)morpholine], and 4-methylpiperazinylethanol), to which it is added slowly over a period of about 10 minutes to 2 hours, preferably about 90 minutes. The end product of Formula I or II is isolated and purified by conventional procedures.

The Carbodiimide Route

In the second synthetic route, mycophenolic acid or an acylated derivative thereof (i.e., a compound according to Formula A as defined above) is dissolved in an inert solvent, preferably tetrahydrofuran ("THF"), and reacted with a heterocyclic aminoalkanol of Formula B in the presence of a carbodiimide, such as DCC ("dicyclohexylcarbodiimide") or di-p-tolylcarbodiimide. The molar ratio of alcohol to the starting acid is about 1:1. The reaction takes place at atmospheric pressure over a period of about 4–8 hours, preferably over 6 hours. A temperature range from about 10° C. to about reflux temperature, preferably about room temperature may be used. The end product of Formula I or II is isolated and purified in the usual manner.

Formula I where Z is —C(O)$R^1$ or —C(S)$R^4$

The compounds of Formula I where Z is —C(O)$R^1$ or —C(S)$R^4$ (or of Formula II where $Z^1$ is —C(O)$R^9$) are prepared by dissolving mycophenolic acid or a heterocyclic aminoalkylester thereof, [i.e., a compound of Formula A wherein $Z^2$ is hydrogen, and M is hydrogen or a radical of Formula C,

in which m and Y are as defined in the Summary of the Invention] in an inert organic solvent, preferably pyridine, and reacting it with about 1 to 6 molar equivalents, preferably about 3 molar equivalents, of an appropriate acyl halide or anhydride or thiocarbonyl halide or anhydride (e.g., acetic anhydride, thioacetyl chloride, propionyl chloride, pivaloyl chloride or adamantoyl chloride), in the presence of about 1 to 6 molar equivalents, preferably about 3 molar equivalents, of an inorganic base (such as sodium carbonate, potassium bicarbonate or the like) or a tertiary organic base (such as N-methylpiperidine, triethylamine, or preferably pyridine). Certain bases (e.g., pyridine) can also serve as the inert organic solvent. The reaction takes place at a temperature of about 0°-25° C., preferably about 5° C., for about 1-10 hours, preferably about 3 hours. When the reaction is substantially complete, the acylated product is isolated by conventional means.

Formula I where Z is —C(O)—$(CH_2)_n$—$CO_2R^5$

The compounds of Formula I where Z is —C(O)—$(CH_2)_n$—$CO_2R^5$ are prepared by dissolving mycophenolic acid or a heterocyclic aminoalkylester thereof [i.e., a compound of Formula A wherein $Z^2$ is hydrogen, and M is hydrogen or the radical of Formula C] in an inert organic solvent, preferably pyridine, and reacting it with about 1 to 6 molar equivalents, preferably about 3 molar equivalents, of an ester acylhalide of a dicarboxylic acid, i.e., a compound of Formula D halo—C(O)—$(CH_2)_n$—$CO_2R^5$  "D"

in which n and $R^5$ are as defined in the Summary of the Invention, in the presence of about 1 to 6 molar equivalents, preferably about 3 molar equivalents, of an inorganic base (such as sodium carbonate, potassium bicarbonate or the like) or a tertiary organic base (such as N-methylpiperidine, triethylamine, or preferably pyridine). Certain bases (e.g., pyridine) can also serve as the inert organic solvent. The reaction takes place at a temperature of about 0°-25° C., preferably about 5° C., for about 1-10 hours, preferably about 3 hours. When the reaction is substantially complete, the product is isolated by conventional means.

The acyl halides of Formula D, if not commercially available, are prepared from commercially available half esters of dicarboxylic acids. For example, the compounds where halo is Cl can be prepared by reaction with thionyl chloride in an inert solvent. The reaction is discussed in further detail in *Synthetic Organic Chemistry*, by Wagner and Zook, pp 546–547, which is incorporated herein by reference. The half esters of dicarboxylic acids, if not commercially available, can be prepared, for example, by the reaction of the appropriate alcohol and an anhydride formed from a dicarboxylic acid as shown in the reaction scheme below.

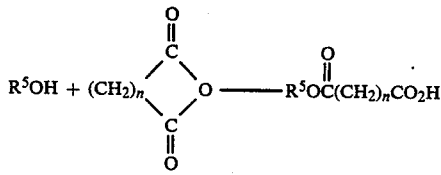

The reaction is discussed in more detail in *Comprehensive Organic Chemistry*, Vol. 2, by Barton and Ollis, p 687, which is incorporated herein by reference.

Formula I where Z is —C(O)$NR^2R^3$ or —C(S)$NR^2R^3$

The carbamates and thiocarbamates of Formula I are prepared from mycophenolic acid or a heterocyclic aminoalkylester thereof (i.e., a compound of Formula A wherein $Z^2$ is hydrogen, and M is hydrogen or the radical of Formula C) by converting it to an activated carbonyl or thiocarbonyl derivative of Formula E

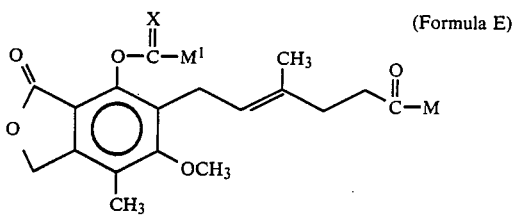

in which X is O or S, $M^1$ is a leaving group chosen to be capable of displacement by an amine (e.g., halo, N-carbonylimidazole, trichloromethoxy, optionally substituted phenoxy, such as 4-methoxyphenyl, 2,4-dichlorophenoxy, and the like) and M is as defined above.

The conversion to the activated carbonyl or thiocarbonyl derivative of Formula E is performed by standard means appropriate to the chosen leaving group. For example, the compound where $M^1$ is chloro is made by reaction of a compound of Formula B with from 1–10 molar equivalents, preferably about 2 molar equivalents, of phosgene or thiophosgene in an inert organic solvent as defined above, preferably benzene. The reaction takes place in the presence of from 1–5 molar equivalents, preferably about 2 molar equivalents of a tertiary organic base such as triethylamine or preferably pyridine. The reaction is conducted at from 0°-50° C., preferably about 25° C., for about 1-72 hours, preferably about 18 hours, and then filtered. Evaporation of the filtrate under vacuum affords the activated carbonyl or thiocarbonyl derivative, where $M^1$ is chloro.

Alternatively, the compound of Formula A is reacted as above, substituting an appropriately substituted alkyl or aryl chloroformate or chlorothioformate for phosgene or thiophosgene, giving the compound of Formula E where $M^1$ is the correspondingly substituted alkoxy or aryloxy moiety.

Similarly, substituting N,N'-carbonyldiimidazole or N,N'-thiocarbonyldiimidazole for phosgene or thiophosgene, gives the compound of Formula E where $M^1$ is N-carbonylimidazole or N-thiocarbonylimidazole.

The products of the reactions described herein can be isolated and purified by any suitable separation or purification procedure, such as, for example, filtration, extraction, crystallization, column chromatography, thin-layer chromatography, thick-layer chromatography, preparative low or high pressure liquid chromatography, or a combination of these procedures. Specific illustrations are described in the Examples. However, other equivalent separation or purification procedures can be used.

The salt products are also isolated by conventional means. For example, the reaction mixtures can be evaporated to dryness and the salts then further purified by standard methods such as those listed above.

The compounds of Formula E are then converted to the desired compounds of Formula I by treatment with an appropriate amine of Formula F,

H—$NR^2R^3$  "F"

in which $R^2$ and $R^3$ are as defined in the Summary of the Invention, to give the corresponding carbamate or thiocarbamate. To carry out this process, the compound of Formula E is dissolved in an inert organic solvent, preferably tetrahydrofuran, and reacted with from about 2-5 molar equivalents, preferably about 2-3 molar equivalents, of the appropriate amine of Formula F dissolved in an inert solvent, preferably tetrahydrofuran. The reaction takes place at a temperature of about 0°-40° C., preferably about 25° C., for about 1-10 hours, preferably about 4 hours, at a pressure of about 1-5 atmospheres, preferably at atmospheric pressure. When the reaction is substantially complete, the product compound of Formula I is isolated by conventional means and, if desired, converted to a pharmaceutically acceptable salt.

Alternatively, the reaction is carried out in the presence of from 1-5 molar equivalents, preferably 2 molar equivalents, of a tertiary organic base or an inorganic base, as defined above. The compound of Formula E is reacted with from 1-4 molar equivalents, preferably about 1.2 molar equivalents, of the appropriate amine of Formula F in an inert organic solvent, as defined above.

The compounds of Formula F are commercially available, or can be prepared by standard methods known to those skilled in the chemical art. The compounds of Formula F wherein $R^3$ is phenyl having a substituent $COOR^{10}$ where $R^{10}$ is lower alkyl are prepared from the compounds of Formula F where $R^{10}$ is H, for example, by reaction of the appropriate compound of Formula F with an excess of the alcohol $R^{10}OH$ (where $R^{10}$ is other than H) in the presence of an acid catalyst. The reaction is described in greater detail in *Organic Functional Group Preparations*, 2nd Edition, Vol. I, by Sandler and Karo, pp. 289-309, which is incorporated herein by reference.

In another synthetic process, the carbamates and thiocarbamates of Formula I are made directly from compounds of Formula A by reaction with an appropriately substituted carbamoyl or thiocarbamoyl chloride of Formula G $$Cl-C(X)NR^2R^3 \qquad \text{"G"}$$

in which X is O, or S, and $R^2$ and $R^3$ are as defined in the Summary of the Invention. To carry out this process, the compound of Formula A is dissolved in an inert organic solvent, preferably tetrahydrofuran, and reacted with from 1-4 molar equivalents, preferably about 1.2 molar equivalents, of the appropriate carbamoyl or thiocarbamoyl chloride of Formula G in the presence of a tertiary organic base or inorganic base as defined above. The reaction takes place at a temperature of about 0°-40° C., preferably about 25° C., for about 1-10 hours, preferably about 4 hours. When the reaction is substantially complete, the desired product of Formula I is isolated by conventional means.

The compounds of Formula G are either available commercially or can be prepared by, for example, reaction of a secondary amine of Formula F with phosgene (X=O) or thiophosgene (X=S). Compounds of Formula G where $R^2$ is H can be prepared by the reaction of an isocyanate or isothiocyanate of Formula H with an excess of dry hydrochloric acid in an inert solvent. These reactions are described in greater detail in *Comprehensive Organic Chemistry*, Vol. 2, by Barton and Ollis, pp. 1088-1090, which is incorporated herein by reference.

The carbamates and thiocarbamates of Formula I where $R^2$ is hydrogen can be made by reacting a compound of Formula A with an appropriately substituted isocyanate or isothiocyanate of Formula H $$R^3NC=X \qquad \text{"H"}$$

in which X is O or S and $R^3$ is as defined in the Summary of the Invention. To carry out this process, the compound of Formula A is dissolved in an inert organic solvent, preferably toluene, and reacted with from 1-5 molar equivalents, preferably about 2 molar equivalents, of the isocyanate or isothiocyanate of Formula H. The reaction takes place at a temperature of about 10°-100° C., preferably about 50° C., for about 1-10 hours, preferably about 4 hours. When the reaction is substantially complete, the product of Formula I is isolated by conventional means.

The compounds of Formula H that are not commercially available are prepared by reaction of an appropriately substituted primary amine ($R^3NH_2$) with phosgene or thiophosgene. The reaction is discussed in further detail in *Organic Functional Group Preparations*, 2nd Edition, Vol. 1, by Sandler and Karo, pp. 364-365, which is incorporated herein by reference.

Formula I Where Z Is $-CR^6=CH-R^7$

The alkenyloxy derivatives of Formula I are prepared from mycophenolic acid or a heterocyclic aminoalkylester thereof (i.e., a compound of Formula A wherein $Z^2$ is hydrogen, and M is hydrogen or the radial of Formula C) by reaction with an appropriately substituted acetylene of Formula J.

$$R^6-C\equiv C-R^7 \qquad \text{"J"}$$

To carry out this process, the compound of Formula A is dissolved in an inert organic solvent as defined above, preferably tetrahydrofuran, and reacted with about 1 to 5 molar equivalents, preferably about 2 molar equivalents, of the appropriate compound of Formula J in the presence of about 1 to 5 molar equivalents, preferably about 2 molar equivalents, of a tertiary organic base or inorganic base as defined above, preferably pyridine. The reaction takes place at a temperature of about 0°-50° C., preferably about 5° C., for about 1-48 hours, preferably about 16 hours. When the reaction is substantially complete, the product is isolated by conventional means.

Acetylenes of Formula J are commercially available or are prepared from propiolic acid or acetylene dicarboxylic acid by conventional esterification procedures, which are discussed in more detail in *Organic Functional Group Preparations*, 2nd Edition, Vol 1, by Sandler and Karo, pp 289-309, which is incorporated herein by reference.

Salts of Compounds of Formulae I and II

Some of the compounds of Formula I may be converted to corresponding base addition salts by virtue of the presence of a carboxylic acid group. THe conversion is accomplished by treatment with a stoichiometric amount of an appropriate base, such as potassium carbonate, sodium bicarbonate, ammonia, ethylenediamine, monoethanolamine, diethanolamine, triethanolamine and the like. Typically, the free acid is dissolved in a polar organic solvent such as ethanol, methanol or ethyl acetate, and the base added in water, ethanol, methanol or isopropanol. The temperature is maintained at 0°-50° C. The resulting salt precipitates spontaneously or may be brought out of solution with a less polar solvent.

The base addition salts of the compounds of Formula I may be decomposed to the corresponding free acids by treating with at least a stoichiometric amount of a suitable acid, such as hydrochloric acid or sulfuric acid, typically in the presence of aqueous solvent, and at a temperature of between 0° and 50° C. The free acid form is isolated by conventional means, such as extraction with an organic solvent.

In like fashion, some of the compounds of Formulae I and II may be converted to the acid addition salts by the substitution of an organic or inorganic acid for the base in the above procedure. The acid salts can be decomposed to the corresponding free bases by similar treatment with an appropriate base.

A dibasic acid, such as sulfuric acid, can form two salts with the compounds of this invention. One such salt, in which one mole of the base and one mole of the acid are present, is called the bisulfate (or hydrogen sulfate) salt. The other, in which two moles of the base and one mole of the acid are present, is called the sulfate.

Preferred Processes

The compounds of the present invention can be prepared according to the following last steps:

a 4-substituted derivative of E-6-(1,3-dihydro-4-hydroxy-6-methoxy-7-methyl-3-oxo-5-isobenzofuranyl)-4-methyl-4-hexenoyl halide of Formula A (where $Z^2$ is not hydrogen and M is halo) is condensed with a heterocyclic aminoalkanol of Formula B to give a compound according to Formula I or according to Formula II where $Z^1$ is not hydrogen;

a 4-substituted derivative of E-6-(1,3-dihydro-4-hydroxy-6-methoxy-7-methyl-3-oxo-5-isobenzofuranyl)-4-methyl-4-hexenoic acid of Formula A (where $Z^2$ is not hydrogen and M is —OH) is contacted with a heterocyclic aminoalkanol of Formula B in the presence of a carbodiimide to give a compound according to Formula I or according to Formula II where $Z^1$ is not hydrogen;

an E-6-(1,3-dihydro-4-hydroxy-6-methoxy-7-methyl-3-oxo-5-isobenzofuranyl)-4-methyl-4-hexenoyl halide of Formula A (where $Z^2$ is hydrogen and M is halo) is condensed with a heterocyclic aminoalkanol of Formula B to give a compound according to Formula II where $Z^1$ is hydrogen;

an E-6-(1,3-dihydro-4-hydroxy-6-methoxy-7-methyl-3-oxo-5-isobenzofuranyl)-4-methyl-4-hexenoic acid of Formula A (where $Z^2$ is not hydrogen and M is —OH) is contacted with a heterocyclic aminoalkanol of Formula B in the presence of a carbodiimide to give a compound according to Formula II where $Z^1$ is hydrogen;

a heterocyclic aminoalkyl E-6-(1,3-dihydro-4-hydroxy-6-methoxy-7-methyl-3-oxo-5-isobenzofuranyl)-4-methyl-4-hexenoate of Formula A (where $Z^2$ is hydrogen and M is a radical of Formula C) is contacted with an acyl halide or anhydride to give a compound according to Formula I where Z is —C(O)$R^1$ or Formula II $Z^1$ is —C(O)$R^9$;

a heterocyclic aminoalkyl E-6-(1,3-dihydro-4-hydroxy-6-methoxy-7-methyl-3-oxo-5-isobenzofuranyl)-4-methyl-4-hexenoate of Formula A (where $Z^2$ is hydrogen and M is a radical of Formula C) is contacted with an thiocarbonyl halide or anhydride to give a compound according to Formula I where Z is —C(S)$R^1$;

a heterocyclic aminoalkyl E-6-(1,3-dihydro-4-hydroxy-6-methoxy-7-methyl-3-oxo-5-isobenzofuranyl)-4-methyl-4-hexenoate of Formula A (where $Z^2$ is hydrogen and M is a radical of Formula C) is contacted with a carboalkyloxyalkanoyloxy halide of Formula D to give a compound according to Formula I where Z is —C(O)—(CH$_2$)$_n$—CO$_2$$R^5$;

a compound of Formula E (where M is a radical of Formula C) is contacted with an amine of Formula F to give a compound according to Formula I where Z is —C(O)NR$^2$R$^3$ or —C(S)NR$^2$R$^3$;

a heterocyclic aminoalkyl E-6-(1,3-dihydro-4-hydroxy-6-methoxy-7-methyl-3-oxo-5-isobenzofuranyl)-4-methyl-4-hexenoate of Formula A (where $Z^2$ is hydrogen and M is a radical of Formula C) is contacted with an carbamoyl chloride or a thiocarbamoyl chloride of Formula F to give a compound according to Formula I where Z is —C(O)NR$^2$R$^3$ or —C(S)NR$^2$R$^3$;

a heterocyclic aminoalkyl E-6-(1,3-dihydro-4-hydroxy-6-methoxy-7-methyl-3-oxo-5-isobenzofuranyl)-4-methyl-4-hexenoate of Formula A (where $Z^2$ is hydrogen and M is a radical of Formula C) is contacted with an isocyanate or an isothiocyanate of Formula H to give a compound according to Formula I where Z is —C(O)NR$^2$R$^3$ or —C(S)NR$^2$R$^3$ and $R^2$ is hydrogen;

a heterocyclic aminoalkyl E-6-(1,3-dihydro-4-hydroxy-6-methoxy-7-methyl-3-oxo-5-isobenzofuranyl)-4-methyl-4-hexenoate of Formula A (where $Z^2$ is hydrogen and M is a radical of Formula C) is contacted with an appropriately substituted acetylene of Formula J to give a compound according to Formula I where Z is a radical of Formula (d) as defined in the Summary of the Invention;

contacting a pharmaceutically acceptable acid or base with a compound of Formula I or II to form the corresponding acid or base addition salt of Formula I or II;

substituting a pharmaceutically acceptable acid or base addition salt of Formula I or II with another pharmaceutically acceptable acid or base; and contacting an acid or base addition salt of Formula I or II with a base or acid to form the corresponding free base or acid compounds of Formula I or II.

Preferred Compounds

A preferred class of compounds are those according to Formula I where Y is —CH$_2$—CH$_2$—O—CH$_2$—CH$_2$—, i.e., the morpholinoalkyl esters.

Another preferred class of compounds are those according to Formulae I and II where m is 2.

Also preferred are the compounds of Formula I where m is 2, Y is —CH$_2$—CH$_2$—O—CH$_2$—CH$_2$—, and Z is —C(O)$R^1$, especially where $R^1$ is adamantyl, preferably 1-adamantyl, i.e., morpholinoethyl E-6-[1,3-dihydro-4-(1-adamantoyloxy)-6-methoxy-7-methyl-3-oxo-5-isobenzofuranyl]-4-methyl-4-hexenoate.

Utility and Administration

General Utility

The compounds of the present invention, including the pharmaceutically acceptable salts thereof, and the compositions containing them, are useful as immunosuppressive agents, anti-inflammatory agents, anti-tumor agents, anti-viral agents, and anti-psoriatic agents in mammals, whether domestic (cattle, pigs, sheep, goats, horses), pets (cats, dogs), or preferably humans. For example compounds of Formulae I and II are useful for treating rheumatoid arthritis, in which there is an immunologically driven inflammatory process. These compounds can be used both prophylactically (e.g., to prevent allograft rejection) and therapeutically.

Testing

Initial animal screening tests to determine anti-inflammatory activity potential include the adjuvant arthritis assay according to the method of Pearson, *Proc. Soc. Exp. Biol. Med.*, 91:95–101 (1956).

Also, in vitro tests, for example those using synovial explants from patients with rheumatoid arthritis, Dayer, et al., *J. Exp. Med.*, 145:1399–1404 (1977), are useful in determining whether compounds exhibit anti-inflammatory activity.

Autoimmune activity is determined utilizing experimental allergic encephalomyelitis by a modification of a procedure initially described by Grieg, et al., *J. Pharmacol. Exp. Ther.* 173:85 (1970).

Immunosuppressive activity is determined by both in vivo and in vitro procedures. In vivo activity is determined utilizing a modification of the Jerne hemolytic plaque assay, [Jerne, et al., "The agar plaque technique for recognizing antibody producing cells," *Cell-bound Antibodies*, Amos, B. and Kaprowski, H. editors (Wistar Institute Press, Philadelphia) 1963, p. 109]. In vitro activity is determined by an adaptation of the procedure described by Greaves, et al. ["Activation of human T and B lymphocytes by polyclonal mitogens," *Nature*, 248, 698–701 (1974)].

Anti-viral activity is determined by the procedure described by Smee, et al. ["Anti-Herpesvirus Activity of the Acyclic Nucleeoside 9-(1,3-Dihydroxy-2-Propoxymethyl)-Guanine," *Antimicrobial Agents and Chemotherapy*, 23(5), 676–682 (1983)], or as described by Planterose ["Antiviral and cytotoxic effects of mycophenolic acid," *Journal of General Virology*, 4, 629 (1969)].

Tests for systemic activity in psoriasis can be carried out as described by Spatz, et al. ["Mycophenolic acid is psoriasis," *British Journal of Dermatology*, 98, 429 (1978)].

Tests for anti-tumor activity can be performed as described by Carter, et al. ["Mycophenolic acid: an anti-cancer compound with unusual properties," *Nature*, 223, 848 (1969)].

General Administration

Administration of the active compounds of Formulae I or II, in pure form or an appropriate pharmaceutical composition, can be carried out via any of the accepted modes of administration of agents for serving similar utilities. Thus, administration can be, for example, orally, nasally, parenterally or topically, in the form of solid, semi-solid, lyophilized powder or liquid dosage forms, such as for example, tablets, suppositories, pills, capsules, powders, solutions, suspensions, emulsions, creams, lotions, aerosols, ointments or the like, preferably in unit dosage forms suitable for simple administration of precise dosages. The compositions will include a conventional pharmaceutical carrier or excipient and an active compound of Formula I or II and, in addition, may include other medicinal agents, pharmaceutical agents, carriers, adjuvants, etc.

Generally, depending on the intended mode of administration, the pharmaceutically acceptable compositions will contain about 1% to about 99% by weight of the pharmaceutically active compound of this invention and 99% to 1% by weight of suitable pharmaceutical excipients. Preferably, the composition will be about 5 to 75% by weight of a pharmaceutically active compound, with the rest being suitable pharmaceutical excipients.

The preferred manner of administration, for the conditions detailed above, is oral using a convenient daily dosage regimen which can be adjusted according to the degree of affliction. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, gum acacia, polyvinylpyrrolidone, gelatin, cellulose and derivatives thereof, and the like.

The active compounds of Formulas may be formulated into a suppository using, for example, about 0.5% to about 50% active ingredient disposed in a carrier of polyethylene glycols (PEG) [e.g., PEG 1000 (96%) and PEG 4000 (4%)].

Liquid pharmaceutically administerable compositions can, for example, be prepared by dissolving, dispersing, etc. an active compound (about 0.5% to about 20%), as described above, and optional pharmaceutical adjuvants in a carrier, such as, for example, water, saline, aqueous dextrose, glycerol, ethanol and the like, to thereby form a solution or suspension.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see *Remington's Pharmaceutical Sciences*, 16th Ed., (Mack Publishing Company, Easton, Pa., 1980). The composition to be administered will, in any event, contain a quantity of the active compound(s) in a pharmaceutically effective amount for relief of the particular condition being treated when administered in accordance with the teachings of this invention.

Generally, the compounds of the invention are administered in a therapeutically effective amount, i.e., a dosage sufficient to effect treatment, which will vary depending on the individual and condition being treated. Typically, a therapeutically effective daily dose is from 0.02 to 100 mg/kg of body weight per day of the active compound of Formulae I or II. Most conditions respond to treatment comprising a dosage level on the order of 0.4 to 30 mg/kg of body weight per day, and most preferably about 10 mg/kg/day. Thus, for administration to a 70 kg person, the dosage range would be about 1.4 mg to 7 g per day, preferably about 7.0 to 700 mg per day.

EXAMPLES

The following examples are given to enable those skilled in the art to more clearly understand and to practice the present invention. They should not be considered as a limitation on the scope of the invention, but merely as being illustrative and representative thereof.

EXAMPLE 1

Morpholinoethyl E-6-(1,3-dihydro-4-hydroxy-6-methoxy-7-methyl-3-oxo-5-isobenzofuranyl)-4-methyl-4-hexenoate 1A. Formula A Where M is Morpholinoethyl and $Z^2$ is H E-6-(1,3-dihydro-4-hydroxy-6-methoxy-7-methyl-3-oxo-5-isobenzofuranyl)-4-methyl-4-hexenoic acid (mycophenolic acid) (32.0 g) was dissolved in dichloromethane (250 ml), followed by the addition of thionyl chloride (25.0 ml) and dimethylformamide (0.3 ml). The reaction mixture was stirred at room temperature for 3 hours, after which the volatile components were removed under vacuum to afford E-6-(1,3-dihydro-4-hydroxy-6-methoxy-7-methyl-3-oxo-5-isobenzofuranyl)-4-methyl-4-hexenoic acid chloride as an oil.

A solution of morpholinoethanol (30.5 ml) in dichloromethane (250 ml) was chilled to 4° C. on an ice bath. The mycophenolic acid chloride oil was dissolved in dichloromethane (50.0 ml) and added to the chilled solution. After stirring for 90 minutes (at 4° C.), the reaction mixture was washed with water and then with aqueous sodium bicarbonate. The organic solution was dried with sodium sulphate and evaporated to yield morpholinoethyl E-6-(1,3-dihydro-4-hydroxy-6-methoxy-7-methyl-3-oxo-5-isobenzofuranyl)-4-methyl-4-hexenoate (m.p. 93°-94° C.).

1B. Formula II Where $Z^1$ is H, m is 2-4, and $Y^1$ is Other Than —(CH$_2$)$_2$—O—(CH$_2$)$_2$—

Similarly, by following the procedure of part A above and substituting for morpholinoethanol [or N-(2-hydroxyethyl)morpholine] the following materials (which materials may be commercially obtained or prepared by methods known to those skilled in the art):
N-(2-hydroxyethyl)pyrrolidine,
N-(2-hydroxyethyl)isoxazolidine,
N-(2-hydroxyethyl)thiazolidine,
1-(2-hydroxyethyl)imidazolidine,
1-(2-hydroxyethyl)-2-methyl-1,2-pyrazolidine,
N-(2-hydroxyethyl)piperidine,
N-(2-hydroxyethyl)-2-oxazine,
N-(2-hydroxyethyl)-4-thiazine,
N-(2-hydroxyethyl)piperazine,
1-(2-hydroxyethyl)-4-methylpiperazine,
1-(2-hydroxyethyl)-3-methyl-1,3-perhydrodiazine,
N-(2-hydroxyethyl)perhydroazepine,
N-(2-hydroxyethyl)perhydro-2-oxazepine,
N-(2-hydroxyethyl)perhydro-4-thiazepine,
1-(2-hydroxyethyl)-1,2-perhydrodiazepine,
1-(2-hydroxyethyl)-3-ethyl-1,3-perhydrodiazepine,
N-(3-hydroxypropyl)pyrrolidine,
N-(3-hydroxypropyl)piperidine,
N-(3-hydroxypropyl)morpholine,
N-(3-hydroxypropyl)perhydroazepine,
1-(4-hydroxybutyl)pyrazolidine,
N-(4-hydroxybutyl)piperidine,
N-(4-hydroxybutyl)morpholine,
N-(4-hydroxybutyl)-4-thiazine,
N-(4-hydroxybutyl)perhydro-2-oxazepine, and
1-(4-hydroxybutyl)-4-t-butyl-1,4-perhydrodiazepine;
there are obtained the following respective compounds:

2-(pyrrolidin-1-yl)ethyl E-6-(1,3-dihydro-4-hydroxy-6-methoxy-7-methyl-3-oxo-5-isobenzofuranyl)-4-methyl-4-hexenoate,
2-(isoxazolidin-1-yl)ethyl E-6-(1,3-dihydro-4-hydroxy-6-methoxy-7-methyl-3-oxo-5-isobenzofuranyl)-4-methyl-4-hexenoate,
2-(thiazolidin-1-yl)ethyl E-6-(1,3-dihydro-4-hydroxy-6-methoxy-7-methyl-3-oxo-5-isobenzofuranyl)-4-methyl-4-hexenoate,
2-(imidazolidin-1-yl)ethyl E-6-(1,3-dihydro-4-hydroxy-6-methoxy-7-methyl-3-oxo-5-isobenzofuranyl)-4-methyl-4-hexenoate,
2-(2-methyl-1,2-pyrazolidin-1-yl)ethyl E-6-(1,3-dihydro-4-hydroxy-6-methoxy-7-methyl-3-oxo-5-isobenzofuranyl)-4-methyl-4-hexenoate,
2-(piperidin-1-yl)ethyl E-6-(1,3-dihydro-4-hydroxy-6-methoxy-7-methyl-3-oxo-5-isobenzofuranyl)-4-methyl-4-hexenoate,
2-(2-oxazin-1-yl)ethyl E-6-(1,3-dihydro-4-hydroxy-6-methoxy-7-methyl-3-oxo-5-isobenzofuranyl)-4-methyl-4-hexenoate,
2-(4-thiazin-1-yl)ethyl E-6-(1,3-dihydro-4-hydroxy-6-methoxy-7-methyl-3-oxo-5-isobenzofuranyl)-4-methyl-4-hexenoate,
2-(piperazin-1-yl)ethyl E-6-(1,3-dihydro-4-hydroxy-6-methoxy-7-methyl-3-oxo-5-isobenzofuranyl)-4-methyl-4-hexenoate,
2-(4-methylpiperazin-1-yl)ethyl E-6-(1,3-dihydro-4-hydroxy-6-methoxy-7-methyl-3-oxo-5-isobenzofuranyl)-4-methyl-4-hexenoate,
2-(3-methyl-1,3-perhydrodiazin-1-yl)ethyl E-6-(1,3-dihydro-4-hydroxy-6-methoxy-7-methyl-3-oxo-5-isobenzofuranyl)-4-methyl-4-hexenoate,
2-(perhydroazepin-1-yl)ethyl E-6-(1,3-dihydro-4-hydroxy-6-methoxy-7-methyl-3-oxo-5-isobenzofuranyl)-4-methyl-4-hexenoate,
2-(perhydro-2-oxazepin-1-yl)ethyl E-6-(1,3-dihydro-4-hydroxy-6-methoxy-7-methyl-3-oxo-5-isobenzofuranyl)-4-methyl-4-hexenoate,
2-(perhydro-4-thiazepin-1-yl)ethyl E-6-(1,3-dihydro-4-hydroxy-6-methoxy-7-methyl-3-oxo-5-isobenzofuranyl)-4-methyl-4-hexenoate,
2-(1,2-perhydrodiazepin-1-yl)ethyl E-6-(1,3-dihydro-4-hydroxy-6-methoxy-7-methyl-3-oxo-5-isobenzofuranyl)-4-methyl-4-hexenoate,
2-(3-ethyl-1,3-perhydrodiazepin-1-yl)ethyl E-6-(1,3-dihydro-4-hydroxy-6-methoxy-7-methyl-3-oxo-5-isobenzofuranyl)-4-methyl-4-hexenoate,
3-(pyrrolidin-1-yl)propyl E-6-(1,3-dihydro-4-hydroxy-6-methoxy-7-methyl-3-oxo-5-isobenzofuranyl)-4-methyl-4-hexenoate,
3-(piperidin-1-yl)propyl E-6-(1,3-dihydro-4-hydroxy-6-methoxy-7-methyl-3-oxo-5-isobenzofuranyl)-4-methyl-4-hexenoate,
3-(morpholin-1-yl)propyl E-6-(1,3-dihydro-4-hydroxy-6-methoxy-7-methyl-3-oxo-5-isobenzofuranyl)-4-methyl-4-hexenoate,
3-(perhydroazepin-1-yl)propyl E-6-(1,3-dihydro-4-hydroxy-6-methoxy-7-methyl-3-oxo-5-isobenzofuranyl)-4-methyl-4-hexenoate,
4-(pyrazolidin-1-yl)butyl E-6-(1,3-dihydro-4-hdroxy-6-methoxy-7-methyl-3-oxo-5-isobenzofuranyl)-4-methyl-4-hexenoate,
4-(piperidin-1-yl)butyl E-6-(1,3-dihydro-4-hydroxy-6-methoxy-7-methyl-3-oxo-5-isobenzofuranyl)-4-methyl-4-hexenoate, 4-(morpholin-1-yl)butyl E-6-(1,3-dihydro-4-hydroxy-6-methoxy-7-methyl-3-oxo-5-isobenzofuranyl)-4-methyl-4-hexenoate, 4-(4-thiazin-1-yl)butyl E-6-(1,3-dihydro-4-hydroxy-6-methoxy-7-methyl-3-oxo-5-isobenzofuranyl)-4-methyl-4-hexenoate, 4-(perhydro-2-oxazepin-1-yl)butyl E-6-(1,3-dihydro-4-hydroxy-6-methoxy-7-methyl-3-oxo-5-isobenzofuranyl)-4-methyl-4-hexenoate, and 4-(4-t-butyl-1,4-perhydrodiazepin-1-yl)butyl E-6-(1,3-dihydro-4-hydroxy-6-methoxy-7-methyl-3-oxo-5-isobenzofuranyl)-4-methyl-4-hexenoate.

1C. Formula I Where Z is Formula (a)

Similarly, by following the procedure of part A above and substituting for E-6-(1,3-dihydro-4-hydroxy-6-methoxy-7-methyl-3-oxo-5-isobenzofuranyl)-4-methyl-4-hexenoic acid the following materials (which materials may be commercially obtained or prepared as described above or by methods known to those skilled in the art):

(E)-6-(1,3-dihydro-4-heptanoyloxy-6-methoxy-7-methyl-3-oxo-5-isobenzofuranyl)-4-methyl-4-hexenoic acid, (E)-6-{1,3-dihydro-4-[N-(4-carbomethoxyphenyl)carbamoyl-oxy]-6-methoxy-7-methyl-3-oxo-5-isobenzofuranyl}-4-methyl-4-hexenoic acid, (E)-6-[1,3-dihydro-4-(N,N-diethylcarbamoyloxy)-6-methoxy-7-methyl-3-oxo-5-isobenzofuranyl]-4-methyl-4-hexenoic acid, (E)-6-[1,3-dihydro-4-(N-methyl-N-isobutylcarbamoyloxy)-6-methoxy-7-methyl-3-oxo-5-isobenzofuranyl]-4-methyl-4-hexenoic acid, and (E)-6-{1,3-dihydro-4-[N-(4-carboethoxyphenyl)-N-ethylcarbamoyloxy]-6-methoxy-7-methyl-3-oxo-5-isobenzofuranyl}-4-methyl-4-hexenoic acid;

there are obtained the following respective compounds:

morpholinoethyl (E)-6-(1,3-dihydro-4-heptanoyloxy-6-methoxy-7-methyl-3-oxo-5-isobenzofuranyl)-4-methyl-4-hexenoate, morpholinoethyl (E)-6-{1,3-dihydro-4-[N-(4-carbomethoxyphenyl)carbamoyloxy]-6-methoxy-7-methyl-3-oxo-5-isobenzofuranyl}-4-methyl-4-hexenoate, morpholinoethyl (E)-6-[1,3-dihydro-4-(N,N-diethylcarbamoyloxy)-6-methoxy-7-methyl-3-oxo-5-isobenzofuranyl]-4-methyl-4-hexenoate, morpholinoethyl (E)-6-[1,3-dihydro-4-(N-methyl-N-isobutylcarbamoyloxy)-6-methoxy-7-methyl-3-oxo-5-isobenzofuranyl]-4-methyl-4-hexenoate, and morpholinoethyl (E)-6-{1,3-dihydro-4-[N-(4-carboethoxyphenyl)-N-ethylcarbamoyloxy]-6-methoxy-7-methyl-3-oxo-5-iso-benzofuranyl}-4-methyl-4-hexenoate.

1D. Formula I Where Z is Formula (b)

Similarly, by following the procedure of part A above and substituting for E-6-(1,3-dihydro-4-hydroxy-6-methoxy-7-methyl-3-oxo-5-isobenzofuranyl)-4-methyl-4-hexenoic acid the following materials (which materials may be commercially obtained or prepared as described above or by methods known to those skilled in the art):

(E)-6-(1,3-dihydro-4-thiopropionoyloxy-6-methoxy-7-methyl-3-oxo-5-isobenzofuranyl)-4-methyl-4-hexenoic acid, (E)-6-(1,3-dihydro-4-thiopivaloyloxy-6-methoxy-7-methyl-3-oxo-5-isobenzofuranyl)-4-methyl-4-hexenoic acid, (E)-6-(1,3-dihydro-4-thioheptanoyloxy-6-methoxy-7-methyl-3-oxo-5-isobenzofuranyl)-4-methyl-4-hexenoic acid, (E)-6-(1,3-dihydro-4-thiobenzoyloxy-6-methoxy-7-methyl-3-oxo-5-isobenzofuranyl)-4-methyl-4-hexenoic acid, (E)-6-{1,3-dihydro-4-[N-(4-carbomethoxyphenyl)thiocarbamoyloxy]-6-methoxy-7-methyl-3-oxo-5-isobenzofuranyl}-4-methyl-4-hexenoic acid, (E)-6-[1,3-dihydro-4-(N,N-diethylthiocarbamoyloxy)-6-methoxy-7-methyl-3-oxo-5-isobenzofuranyl]-4-methyl-4-hexenoic acid, (E)-6-[1,3-dihydro-4-(N-methyl-N-isobutylthiocarbamoyloxy)-6-methoxy-7-methyl-3-oxo-5-isobenzofuranyl]-4-methyl-4-hexenoic acid, and (E)-6-{1,3-dihydro-4-[N-(4-carboethoxyphenyl)-N-ethylthiocarbamoyloxy]-6-methoxy-7-methyl-3-oxo-5-isobenzofuranyl}-4-methyl-4-hexenoic acid;

there are obtained the following respective compounds:

morpholinoethyl(E)-6-(1,3-dihydro-4-thiopropionoyloxy-6-methoxy-7-methyl-3-oxo-5-isobenzofuranyl)-4-methyl-4-hexenoate, morpholinoethyl (E)-6-(1,3-dihydro-4-thiopivaloyloxy-6-methoxy-7-methyl-3-oxo-5-isobenzofuranyl)-4-methyl-4-hexenoate, morpholinoethyl (E)-6-(1,3-dihydro-4-thioheptanoyloxy-6-methoxy-7-methyl-3-oxo-5-isobenzofuranyl)-4-methyl-4-hexenoate, morpholinoethyl (E)-6-(1,3-dihydro-4-thiobenzoyloxy-6-methoxy-7-methyl-3-oxo-5-isobenzofuranyl)-4-methyl-4-hexenoate, morpholinoethyl (E)-6-{1,3-dihydro-4-[N-(4-carboethoxyphenyl)thiocarbamoyloxy]-6-methoxy-7-methyl-3-oxo-5-isobenzofuranyl}-4-methyl-4-hexenoate, morpholinoethyl (E)-6-[1,3-dihydro-4-(N,N-diethylthiocarbamoyloxy)-6-methoxy-7-methyl-3-oxo-5-isobenzofuranyl]-4-methyl-4-hexenoate, morpholinoethyl (E)-6-[1,3-dihydro-4-(N-methyl-N-isobutylthiocarbamoyloxy)-6-methoxy-7-methyl-3-oxo-5-isobenzofuranyl]-4-methyl-4-hexenoate, and morpholinoethyl (E)-6-{1,3-dihydro-4-[N-(4-carboethoxyphenyl)-N-ethylthiocarbamoyloxy]-6-methoxy-7-methyl-3-oxo-5-iso-benzofuranyl}-4-methyl-4-hexenoate.

1E. Formula I Where Z is Formula (c)

Similarly, by following the procedure of part A above and substituting for E-6-(1,3-dihydro-4-hydroxy-6-methoxy-7-methyl-3-oxo-5-isobenzofuranyl)-4-methyl-4-hexenoic acid the following materials (which materials may be commercially obtained or prepared as described above or by methods known to those skilled in the art):

(E)-6-[1,3-dihydro-4-(carboethoxycarbonyloxy)-6-methoxy-7-methyl-3-oxo-5-isobenzofuranyl]-4-methyl-4-hexenoic acid, (E)-6-[1,3-dihydro-4-(carbomethoxyethanoyloxy)-6-methoxy-7-methyl-3-oxo-5-isobenzofuranyl]-4-methyl-4-hexenoic acid, (E)-6-[1,3-dihydro-4-(carboethoxyethanoyloxy)-6-methoxy-7-methyl-3-oxo-5-isobenzofuranyl]-4-methyl-4-hexenoic acid, (E)-6-[1,3-dihydro-4-(3-carbomethoxypropionyloxy)-6-methoxy-7-methyl-3-oxo-5-isobenzofuranyl]-4-methyl-4-hexenoic acid, (E)-6-[1,3-dihydro-4-(3-carboethoxypropionyloxy)-6-methoxy-7-methyl-3-oxo-5-isobenzofuranyl]-4-methyl-4-hexenoic acid, (E)-6-[1,3-dihydro-4-(4-carbomethoxybutanoyloxy)-6-methoxy-7-methyl-3-oxo-5-isobenzofuranyl]-4-methyl-4-hexenoic acid, and (E)-6-[1,3-dihydro-4-(5-carbomethoxypentanoyloxy)-6-methoxy-7-methyl-3-oxo-5-isobenzofuranyl]-4-methyl-4-hexenoic acid;

there are obtained the following respective compounds:

morpholinoethyl (E)-6-[1,3-dihydro-4-(carboethoxycarbonyloxy)-6-methoxy-7-methyl-3-oxo-5-isobenzofuranyl]-4-methyl-4-hexenoate, morpholinoethyl (E)-6-[1,3-dihydro-4-(carbomethoxyethanoyloxy)-6-methoxy-7-methyl-3-oxo-5-isobenzofuranyl]-4-methyl-4-hexenoate, morpholinoethyl (E)-6-[1,3-dihydro-4-(carboethoxyethanoyloxy)-6-methoxy-7-methyl-3-oxo-5-isobenzofuranyl]-4-methyl-4-hexenoate, morpholinoethyl (E)-6-[1,3-dihydro-4-(3-carbomethoxypropionyloxy)-6-methoxy-7-methyl-3-oxo-5-isobenzofuranyl]-4-methyl-4-hexenoate, morpholinoethyl (E)-6-[1,3-dihydro-4-(3-carboethoxypropionyloxy)-6-methoxy-7-methyl-3-oxo-5-isobenzofuranyl]-4-methyl-4-hexenoate, morpholinoethyl (E)-6-[1,3-dihydro-4-(4-carbomethoxybutanoyloxy)-6-methoxy-7-methyl-3-oxo-5-isobenzofuranyl]-4-methyl-4-hexenoate, and morpholinoethyl (E)-6-[1,3-dihydro-4-(5-carbomethoxypentanoyloxy)-6-methoxy-7-methyl-3-oxo-5-isobenzofuranyl]-4-methyl-4-hexenoate.

1F. Formula I Where Z is Formula (d)

Similarly, by following the procedure of part A above and substituting for E-6-(1,3-dihydro-4-hydroxy-6-methoxy-7-methyl-3-oxo-5-isobenzofuranyl)-4-methyl-4-hexenoic acid the following materials (which materials may be commercially obtained or prepared as described above or by methods known to those skilled in the art):

(E)-6-[1,3-dihydro-4-(1,2-dicarbomethoxyeth-(E)-enyloxy)-6-methoxy-7-methyl-3-oxo-5-isobenzofuranyl]-4-methyl-4-hexenoic acid, and (E)-6-[1,3-dihydro-4-(2-carboethoxyeth-(E)-enyloxy)-6-methoxy-7-methyl-3-oxo-5-isobenzofuranyl]-4-methyl-4-hexenoic acid;

there are obtained the following respective compounds:

morpholinoethyl (E)-6-[1,3-dihydro-4-(1,2-dicarbomethoxy-eth-(E)-enyloxy)-6-methoxy-7-methyl-3-oxo-5-isobenzofuranyl]-4-methyl-4-hexenoate, and morpholinoethyl (E)-6-[1,3-dihydro-4-(2-carboethoxyeth-(E)-enyloxy)-6-methoxy-7-methyl-3-oxo-5-isobenzofuranyl]-4-methyl-4-hexenoate.

1G. Formulae I and II where m is 2–4, Z is Formulas (a)–(d), $Z^1$ is Other Than Hydrogen, and Y and $Y^1$ are Other Than —$(CH_2)_2$—O—$(CH_2)_2$—

Similarly, by following the procedure of part A above, substituting the starting materials of part B for morpholinoethanol and substituting the starting materials described in parts C-F for E-6-(1,3-dihydro-4-hydroxy-6-methoxy-7-methyl-3-oxo-5-isobenzofuranyl)-4-methyl-4-hexenoic acid, the corresponding compounds are obtained, such as:

2-(pyrrolidin-1-yl)ethyl E-6-(1,3-dihydro-4-propionyloxy-6-methoxy-7-methyl-3-oxo-5-isobenzofuranyl)-4-methyl-4-hexenoate, 2-(thiazolidin-1-yl)ethyl E-6-[1,3-dihydro-4-(2-methylpropionyloxy)-6-methoxy-7-methyl-3-oxo-5-isobenzofuranyl]-4-methyl-4-hexenoate, 2-(piperidin-1-yl)ethyl E-6-(1,3-dihydro-4-pivaloyloxy-6-methoxy-7-methyl-3-oxo-5-isobenzofuranyl)-4-methyl-4-hexenoate, 3-(morpholin-1-yl)propyl E-6-(1,3-dihydro-4-adamantoyloxy-6-methoxy-7-methyl-3-oxo-5-isobenzofuranyl)-4-methyl-4-hexenoate, 4-(perhydro-2-oxazepin-1-yl)butyl E-6-(1,3-dihydro-4-benzoyloxy-6-methoxy-7-methyl-3-oxo-5-isobenzofuranyl)-4-methyl-4-hexenoate, 2-(4-thiazin-1-yl)ethyl E-6-{1,3-dihydro-4-[N-(4-carbomethoxyphenyl)thiocarbamoyloxy]-6-methoxy-7-methyl-3-oxo-5-isobenzofuranyl}-4-methyl-4-hexenoate, 2-(4-methylpiperazin-1-yl)ethyl E-6-[1,3-dihydro-4-(carbomethoxyethanoyloxy)-6-methoxy-7-methyl-3-oxo-5-isobenzofuranyl]-4-methyl-4-hexenoate, and 4-(4-t-butyl-1,4-perhydroazepin-1-yl)butyl E-6-[1,3-dihydro-4-(1,2-dicarboethoxy-eth-(E)-enyloxy)-6-methoxy-7-methyl-3-oxo-5-isobenzofuranyl]-4-methyl-4-hexenoate.

EXAMPLE 2

Morpholinoethyl E-6-[1,3-dihydro-4-(1-adamantoyloxy)-6-methoxy-7-methyl-3-oxo-5-isobenzofuranyl]-4-methyl-4-hexenoate

2A. Formula I where Z is Adamantoyl

Morpholinoethyl E-6-(1,3-dihydro-4-hydroxy-6-methoxy-7-methyl-3-oxo-5-isobenzofuranyl)-4-methyl-4-hexenoate (10.0 g) was dissolved in pyridine (50.0 ml) followed by the addition of 1-adamantanecarbonyl chloride (10.0 ml). The mixture was stirred at room temperature for 90 minutes, then poured into water and extracted with ethyl acetate. The organic solution was dried and evaporated to give morpholinoethyl E-6-[1,3-dihydro-4-(1-adamantoyloxy)-6-methoxy-7-methyl-3-oxo-5-isobenzofuranyl]-4-methyl-4-hexenoate.

2B. Formula I where Z is Other Than Adamantoyl

Similarly, by following the procedure of part A above and substituting heptanoyl bromide for adamantanecarbonyl chloride, there is obtained morpholinoethyl E-6-(1,3-dihydro-4-heptanoyloxy-6-methoxy-7-methyl-3-oxo-5-isobenzofuranyl)-4-methyl-4-hexenoate.

EXAMPLE 3

Morpholinoethyl (E)-6-(1,3-dihydro-4-carbamoyloxy-6-methoxy-7-methyl-3-oxo-5-isobenzofuranyl)-4-methyl-4-hexenoate To a solution of 500 mgs of morpholinoethyl (E)-6-(1,3-dihydro-4-hydroxy-6-methoxy-7-methyl-3-oxo-5-isobenzofuranyl)-4-methyl-4-hexenoate in 10 ml of benzene cooled in an ice bath is added 0.1 ml of pyridine and 6 ml of a 12.5% solution of phosgene in benzene. The solution is stirred at 25° C. overnight, the precipitate filtered off and solvent removed from the filtrate under reduced pressure. The residue is dissolved in 5 ml of tetrahydrofuran and to this solution is added dropwise a solution of ammonia in tetrahydrofuran until the reaction is complete. The mixture is poured into water and extracted with ethyl acetate. The organic solution is dried over magnesium sulfate and evaporated to an oil which is chromatographed on silica gel, eluting with a 50:1 mixture of dichloromethane and methanol. The purified product is stirred with a mixture of ether and hexane and filtered giving morpholinoethyl (E)-6-(1,3- dihydro-4-carbamoyloxy-6-methoxy-7-methyl-3-oxo-5-isobenzofuranyl)-4-methyl-4-hexenoate.

EXAMPLE 4

3-(Morpholin-1-yl)propyl (E)-6-(1,3-dihydro-4-acetoxy-6-methoxy-7-methyl-3-oxo-5-isobenzofuranyl)-4-methyl-4-hexenoate 4A. Formula II where $Z^1$ is Acetoxy, m is 3, and Y is —(CH$_2$)$_2$—O—(CH$_2$)$_2$—

To a solution of 1.6 g of 3-(morpholin-1-yl)propyl (E)-6-(1,3-dihydro-4-hydroxy-6-methoxy-7-methyl-3-oxo-5-isobenzofuranyl)-4-methyl-4-hexenoate in 120 ml of acetonitrile at 0° C. is added 0.74 ml of pyridine followed by 1.0 ml of acetyl chloride. After stirring for 2 hours the reaction mixture is poured into dilute hydrochloric acid and extracted with ethyl acetate. The organic solution is dried over anhydrous magnesium sulfate and evaporated to an oil, which is triturated with ether to give 3-(morpholin-1-yl)propyl (E)-6-(1,3-dihydro-4-acetoxy-6-methoxy-7-methyl-3-oxo-5-isobenzofuranyl)-4-methyl-4-hexenoate.

4B. Formula I Where Z is Formula (c), m is 3, and Y is —(CH$_2$)$_2$—O—(CH$_2$)$_2$—

Similarly, by following the procedure of part A above and substituting for acetyl chloride the following ester acylhalides of dicarboxylic acid according to Formula D:
carboethoxycarbonylchloride,
carbomethoxyethanoylchloride,
carboethoxyethanoylbromide, and
3-carbomethoxypropionylbromide;
there are obtained the following respective compounds:
3-(morpholin-1-yl)propyl (E)-6-(1,3-dihydro-4-carboethoxycarbonyloxy-6-methoxy-7-methyl-3-oxo-5-isobenzofuranyl)-4-methyl-4-hexenoate,
3-(morpholin-1-yl)propyl (E)-6-(1,3-dihydro-4-carbomethoxyethanoyloxy-6-methoxy-7-methyl-3-oxo-5-isobenzofuranyl)-4-methyl-4-hexenoate,
3-(morpholin-1-yl)propyl (E)-6-(1,3-dihydro-4-carboethoxyethanoyloxy-6-methoxy-7-methyl-3-oxo-5-isobenzofuranyl)-4-methyl-4-hexenoate, and
3-(morpholin-1-yl)propyl (E)-6-[1,3-dihydro-4-(3-carbomethoxypropionyloxy)-6-methoxy-7-methyl-3-oxo-5-isobenzofuranyl]-4-methyl-4-hexenoate.

EXAMPLE 5

Morpholinoethyl E-6-[1,3-dihydro-4-(1,2-dicarbomethoxy-1-(E)-enyloxy)-6-methoxy-7-methyl-3-oxo-5-isobenzofuranyl]-4-methyl-4-hexenoate To a solution of 6.72 g of morpholinoethyl E-6-(1,3-dihydro-4-hydroxy-6-methoxy-7-methyl-3-oxo-5-isobenzofuranyl)-4-methyl-4-hexenoate in 100 ml of tetrahydrofuran at −80° C. is added 3.16 ml of pyridine and 4.8 g of dimethyl acetylenedicarboxylate and the mixture is allowed to warm to 25° C. and was stirred for 16 hours. The solution is poured into dilute hydrochloric acid and extracted with diethyl ether. The organic solution is dried over anhydrous sodium sulfate and the solvent removed under reduced pressure. The residue is chromatographed on silica gel eluting with 50:1 dichloromethane:ethanol. The purified product is recrystallized from diethyl ether/hexane mixture, to yield morpholinoethyl E-6-[1,3-dihydro-4-(1,2-dicarbomethoxyeth-1-(E)-enyloxy)-6-methoxy-7-methyl-3-oxo-5-isobenzofuranyl]-4-methyl-4-hexenoate.

EXAMPLE 6

Morpholinoethyl E-6-(1,3-dihydro-4-carbamoyloxy-6-methoxy-7-methyl-3-oxo-5-isobenzofuranyl)-4-methyl-4-hexenoate 6A. Formula I Where Z is C(O)NH$_2$ To 1.0 g of E-6-(1,3-dihydro-4-carbamoyloxy-6-methoxy-7-methyl-3-oxo-5-isobenzofuranyl)-4-methyl-4-hexenoic acid dissolved in 20 ml of dry THF is added 0.59 g of dicyclohexylcarbodiimide and 0.037 g of N-(2-hydroxyethyl)morpholine. The mixture is left at room temperature for 6 hours, then evaporated to dryness. The residue is chromatographed on silica gel, eluting with 50:1 dichloromethane:methanol, to give morpholinoethyl E-6-(1,3-dihydro-4-carbamoyloxy-6-methoxy-7-methyl-3-oxo-5-isobenzofuranyl)-4-methyl-4-hexenoate.

6B. Formula I Where Z is C(O)NH$_2$

Similarly, by following the procedure of part A above and substituting (E)-6-(1,3-dihydro-4-thiocarbamoyloxy-6-methoxy-7-methyl-3-oxo-5-isobenzofuranyl)-4-methyl-4-hexenoic acid for E-6-(1,3-dihydro-4-carbamoyloxy-6-methoxy-7-methyl-3-oxo-5-isobenzofuranyl)-4-methyl-4-hexenoic acid, there is obtained morpholinoethyl (E)-6-(1,3-dihydro-4-thiocarbamoyl-oxy-6-methoxy-7-methyl-3-oxo-5-isobenzofuranyl)-4-methyl-4-hexenoate.

6C. Formula I Where Z is C(S)NH$_2$

Similarly, by following the procedure of part A above and substituting 3-(pyrrolidin-1-yl)propanol for N-(2-hydroxyethyl)morpholine, there is obtained 3-(pyrrolidin-1-yl)propyl E-6-(1,3-dihydro-4-carbamoyloxy-6-methoxy-7-methyl-3-oxo-5-isobenzofuranyl)-4-methyl-4-hexenoate.

EXAMPLE 7

Morpholinoethyl E-6-(1,3-dihydro-4-adamantoyloxy-6-methoxy-7-methyl-3-oxo-5-isobenzofuranyl)-4-methyl-4-hexenoate hydrochloride 7A. Hydrochloride Salt of Formula I where Z is Adamantoyl Morpholinoethyl E-6-(1,3-dihydro-4-adamantoyloxy-6-methoxy-7-methyl-3-oxo-5-isobenzofuranyl)-4-methyl-4-hexenoate (38.0 g) was dissolved in isopropanol (200 ml) and the solution was added to a solution of hydrogen chloride (10.0 g) in isopropanol (150 ml). The hydrochloride salt was collected by filtration and dried under vacuum (m.p. 192°–194° C.).

7B. Other Hydrochloride Salts of Formulae I and II

Similarly, by following the procedure of part A above and substituting for morpholinoethyl E-6-(1,3-dihydro-4-admantoyloxy-6-methoxy-7-methyl-3-oxo-5-isobenzofuranyl)-4-methyl-4-hexenoate the materials prepared in Examples 1B to 6, the corresponding hydrochloride salts are obtained.

EXAMPLE 8

Morpholinoethyl E-6-(1,3-dihydro-4-adamantoyloxy-6-methoxy-7-methyl-3-oxo-5-isobenzofuranyl)-4-methyl-4-hexenoate bisulfate

8A. Bisulfate Salt of Formula I where Z is Adamantoyl

Morpholinoethyl E-6-(1,3-dihydro-4-hydroxy-6-methoxy-7-methyl-3-oxo-5-isobenzofuranyl)-4-methyl-b 4-hexenoate (4.6 g) is dissolved in ethyl acetate (50 ml) and the solution added to a solution of sulfuric acid (0.79 g) in isopropanol (50 ml). The bisulfate salt is collected by filtration, washed with ethyl acetate and dried under vacuum at 50° C.

8B. Other Bisulfite Salts of Formulae I and II

Similarly, by following the procedure of part A above and substituting for morpholinoethyl E-6-(1,3-dihydro-4-adamantoyloxy-6-methoxy-7-methyl-3-oxo-5-isobenzofuranyl)-4-methyl-4-hexenoate the materials prepared in Examples 1B to 6, the corresponding bisulfate salts are obtained.

EXAMPLE 9

Conversion of Free Acid to Salt

One molar equivalent of sodium hydroxide in water is added to a methanolic solution of 1.0 g of morpholinoethyl (E)-6-[1,3-dihydro-4-(4-carboxyphenylcarbamoyloxy)-6-methoxy-7-methyl-3-oxo-5-isobenzofuranyl]-4-methyl-4-hexenoate. The solvent is removed under vacuum and the residue recrystallized to give the sodium salt of morpholinoethyl (E)-6-[1,3-dihydro-4-(4-carboxyphenylcarbamoyloxy)-6-methoxy-7-methyl-3-oxo-5-isobenzofuranyl]-4-methyl-4-hexenoate.

EXAMPLE 10

Conversion of Salt to Free Acid 1.0 G of the sodium salt of morpholinoethyl (E)-6-[1,3-dihydro-4-(4-carboxyphenylcarbamoyloxy)-6-methoxy-7-methyl-3-oxo-5-isobenzofuranyl]-4-methyl-4-hexenoate suspended in ether is stirred with 1 molar equivalent of dilute aqueous sulfuric acid until the salt is completely dissolved. The organic layer is separated, washed with water, dried over magnesium sulfate and evaporated to yield morpholinoethyl (E)-6-[1,3-dihydro-4-(4-carboxyphenylcarbamoyloxy)-6-methoxy-7-methyl-3-oxo-5-isobenzofuranyl]-4-methyl-4-hexenoate.

EXAMPLE 11

Direct Interchange of Basic Salts 1.0 G of the ammonium salt of morpholinoethyl (E)-6-[1,3-dihydro-4-(4-carboxyphenylcarbamoyloxy)-6-methoxy-7-methyl-3-oxo-5-isobenzofuranyl]-4-methyl-4-hexenoate is dissolved in methanol containing one molar equivalent of sodium hydroxide and the solution evaporated to dryness under vacuum. The residue is recrystallized to give the sodium salt of morpholinoethyl (E)-6-[1,3-dihydro-4-(4-carboxyphenylcarbamoyloxy)-6-methoxy-7-methyl-3-oxo-5-isobenzofuranyl]-4-methyl-4-hexenoate.

EXAMPLE 12

This example illustrates the preparation of a representative pharmaceutical formulation for oral administration containing an active compound of Formula I, e.g., morpholinopropyl E-6-[1,3-dihydro-4-(1-adamantoyloxy)-6-methoxy-7-methyl-3-oxo-5-isobenzofuranyl]-4-methyl-4-hexenoate hydrochloride.

| Ingredients | Quantity per tablet, mgs. |
| --- | --- |
| Active compound | 200 |
| lactose, spray-dried | 148 |
| magnesium stearate | 2 |

The above ingredients are mixed and introduced into a hard-shell gelatin capsule.

Other compounds of Formulae I and II, such as those prepared in accordance with Examples 1-11, can be used as the active compound in the preparation of the orally administrable formulations of this example.

EXAMPLE 13

This example illustrates the preparation of another representative pharmaceutical formulation for oral administration, containing an active compound of Formula I, e.g., morpholinopropyl E-6-[1,3-dihydro-4-(1-adamantoyloxy)-6-methoxy-7-methyl-3-oxo-5-isobenzofuranyl]-4-methyl-4-hexenoate hydrochloride.

| Ingredients | Quantity per tablet, mgs. |
| --- | --- |
| Active compound | 400 |
| cornstarch | 50 |
| lactose | 145 |
| magnesium stearate | 5 |

The above ingredients are mixed intimately and pressed into single scored tablets.

Other compounds of Formulae I and II, such as those prepared in accordance with Examples 1-11, can be used as the active compound in the preparation of the orally administrable formulations of this example.

EXAMPLE 14

This example illustrates the preparation of a representative pharmaceutical formulation containing an active compound of Formula I, e.g., morpholinopropyl E-6-[1,3-dihydro-4-(1-adamantoyloxy)-6-methoxy-7-methyl-3-oxo-5-isobenzofuranyl]-4-methyl-4-hexenoate hydrochloride.

An oral suspension is prepared having the following composition:

| Ingredients | |
| --- | --- |
| Active compound | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Other compounds of Formulae I and II, such as those prepared in accordance with Examples 1-11, can be used as the active compound in the preparation of the orally administrable formulations of this example.

EXAMPLE 15

This example illustrates the preparation of a representative pharmaceutical formulation containing an active compound of Formula I, e.g., morpholinopropyl E-6-[1,3-dihydro-4-(1-adamantoyloxy)-6-methoxy-7-methyl-3-oxo-5-isobenzofuranyl]-4-methyl-4-hexenoate hydrochloride.

an injectable preparation buffered to a pH of 4 is prepared having the following composition:

| Ingredients | |
|---|---|
| Active compound | 0.2 g |
| Sodium Acetate Buffer Solution (0.4 M) | 2.0 ml |
| HCl (1N) | q.s. to pH 4 |
| water (distilled, sterile) | q.s. to 20 ml |

Other compounds of Formulae I and II, such as those prepared in accordance with Examples 1-11, can be used as the active compound in the preparation of the injectable formulations of this example.

EXAMPLE 16

This example illustrates the preparation of a representative pharmaceutical formulation for topical application containing an active compound of Formula I, e.g., morpholinopropyl E-6-[1,3-dihydro-4-(1-adamantoyloxy)-6-methoxy-7-methyl-3-oxo-5-isobenzofuranyl]-4-methyl-4-hexenoate hydrochloride.

| Ingredients | grams |
|---|---|
| Active compound | 0.2-10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Other compounds of Formulae I and II, such as those prepared in accordance with Examples 1-11, can be used as the active compound in the preparation of the topical formulations of this example.

EXAMPLE 17

This example illustrates the preparation of a representative pharmaceutical formulation containing an active compound of Formula I, e.g., morpholinopropyl E-6-[1,3-dihydro-4-(1-adamantoyloxy)-6-methoxy-7-methyl-3-oxo-5-isobenzofuranyl]-4-methyl-4-hexenoate hydrochloride.

A suppository totalling 2.5 grams is prepared having the following composition:
Active compound: 500 mg
witepsol H-15*: balance
(*triglycerides of saturated vegetable fatty acid; a product of Riches-Nelson, Inc., New York, N.Y.).

Other compounds of Formulae I and II, such as those prepared in accordance with Examples 1-11, can be used as the active compound in the preparation of the suppository formulations of this example.

EXAMPLE 18

Determination of Anti-Inflammatory Activity Utilizing Adjuvant-Induced Arthritis In The Rat Protocol:

This procedure is a modification of a procedure initially described by Pearson, C. M., *Proc. Soc. Exp. Biol. Med.*, 91:95-101 (1956).

Female Simonsen albino rats weighing 160-180 g receive 0.1 ml of a suspension in paraffin oil of heat-killed M. *Mycobacterium butyricum* (10 mg/ml) by means of an intradermal injection into the proximal ⅔ of the tail on day 0. Beginning on day 1, the test material is administered orally in an aqueous vehicle (0.5 ml/dose) twice each day for 17 days. On day 18 the intensity of the swelling of the four foot pads and tail is determined utilizing a scoring system in which the swelling in the four paws was scored 0-4 for each paw and the tail swelling is scored 0-3, such that the total maximum score is 19.

The compounds of the present invention show anti-inflammatory activity when tested by this method.

EXAMPLE 19

Determination of Autoimmune Activity Utilizing Experimental Allergic Encephalomyelitis Protocol:

This procedure is a modification of a procedure initially described by Grieg, et al., [J. Pharmacol. Exp. Ther. 173:85 (1970).

On day 1, Experimental Allergic Encephalomyelitis is induced by giving an 0.1 ml sub-plantar injection into the dorsum of the right hand paw of an emulsion consisting of 15 mg (wet weight) of syngeneic spinal cord tissue, 0.06 ml of Freund's Incomplete Adjuvant (Difco), 0.04 ml of sterile 0.9% saline, and 0.2 mg of heat killed and dried *Mycobacterium butyricum (Difco)*. On days 12-17, clinical evaluations are obtained for each animal. The animals are considered positive if flaccid hind limb paralysis is present on one or more days.

The compounds of the present invention show autoimmune activity when tested by this method.

EXAMPLE 20

Determination of Immunosuppressive Activity Utilizing The Hemolytic Plaque Forming Cell Assay This procedure is a modification of "The agar plaque technique for recognizing antibody producing cells," a procedure initially described by Jerne, et al. [*Cellbound Antibodies*, Amos and Kaprowski editors (Wistar Institute Press, Philadelphia, 1963) p. 109].

Groups of 5-6 adult C578B1/6 male mice were sensitized with $1 \times 10^8$ sheep red blood cells ("SRBC") and simultaneously treated with an oral dosage form of the test material in an aqueous vehicle. Animals in a control group receive the same volume of vehicle. Four days after SRBC inoculation, spleens are dispersed in loose Ten Broeck homogenizers. The number of nucleated cells ("WBC") is determined and the spleen cell suspension is mixed with SRBC, guinea pig complement and agar solution at 0.5% concentration. Aliquots of the above mixture (0.1 ml) are dropped on four separate quadrants of a Petri dish and are covered with cover slips. After two hours incubation at 37° C., areas of hemolysis around plaque-forming cells ("PFC") are counted with a dissecting microscope. Total WBC/spleen, PFC/spleen and PFC/10⁶ WBC ("PPM") are calculated for each mouse spleen. Geometric means of each treatment group are then compared with the vehicle-treated control group.

The compounds of the present invention show immunosuppressive activity when tested by this method.

EXAMPLE 21

Determination of Immunosuppressive Activity Utilizing Responses of Human Peripheral Blood Lymphocytes to T- and B-cell Mitogens This procedure is a modification of a procedure initially described by Greaves, et al. ["Activation of human T and B lymphocytes by polyclonal mitogens," *Nature*, 248, 698–701 (1974)].

Human mononuclear cells ("PBL") are separated from heparinized whole blood by density gradient centrifugation in Ficoll-Paque (Pharmacia). After washing, $2\times10^5$ cells/well are cultured in microtiter plates with RPMI 1640 supplemented with 5% fetal calf serum, penicillin and streptomycin. To evaluate differential effects on T- and B-lymphocytes, different mitogens are used: PHA (Sigma) at 10 µg/ml, PWM (Sigma) at 20 µg/ml and Staphylococcus Protein A bound to Sepharose (SPA) (Sigma) 2 mg/ml or 14 µg/ml of Protein A. Test materials are tested at concentrations between $10^4$ and $10^8$M, by addition to the culture at time 0. Cultures are set up in quadruplicate and incubated at 37° C. in a humidified atmosphere with 7% $CO_2$ for 72 hours. A pulse of 0.5 µCi/well of ³H-thymidine is added for the last 6 hours. Cells are collected on glass fiber filters with an automatic harvester and radioactivity is measured by standard scintillation procedures. The 50% inhibitory concentration ("IC₅₀") for mitogenic stimulation is determined graphically.

The compounds of the present invention show immunosuppressive activity when tested by this method.

EXAMPLE 22

Determination of Anti-viral Activity Utilizing 50% Plaque Reduction Assay

This procedure is described by Smee, et al., in "Anti-Herpesvirus Activity of the Acyclic Nucleoside 9-(1,3-Dihydroxy-2-Propoxymethyl)Guanine" [*Antimicrobial Agents and Chemotherapy*, 23(5), 676–682 (1983)].

Confluent monolayers of Vero cells in six-well Costar microplates (Bellco Glass, Inc., Vineland, N.J.) are infected with 100 to 200 PFU of HSV or pseudorabies virus. After a 1.25 hour adsorption period, the virus is aspirated and EMEM containing 0.6% methylcellulose, 2% fetal bovine serum, 0.25% $NaHCO_3$, 10 mM HEPES buffer, 50 µg of gentamicin per ml, and the test compound are applied. Three wells per dilution of the test compound, and six control wells without test compound are incubated for four days at 37° C. in 5% $CO_2$, after which the methylcellulose layer is removed and the cells are fixed with methanol for 10 minutes and stained with 10% Giemsa stain (Fisher Scientific Co., Fair Lawn, N.J.) for 20 minutes. After the plates are aspirated and dried, the plaques are counted at 13× magnification with a Bellco plaque viewer. Drug concentrations that reduced plaque numbers by 50% [the 50% inhibitory dose (ID₅₀)] are calculated, e.g., with a computer using a semilog probit analysis program [see Finney, D. J., *Probit analysis*, 3rd Ed., p. 333, (Cambridge University Press, London, 1971)].

The compounds of the present invention show anitviral activity when tested by this method.

EXAMPLE 23

Bioavailability—Plasma Levels

Compounds of Formula I or II are given to four male cynomolgus monkeys as a solid dosage form (about 20 mg/kg body weight) with one-week intervals between doses. Mycophenolic acid is given to as control group. The compounds are weighed into hard gelatin capsules and administered orally. Samples of plasma are obtained at 0.25, 0.5, 1, 3, 5, 7 and 24 hours after dosing, and are analyzed for concentrations of mycophenolic acid by HPLC.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound represented by the formula:

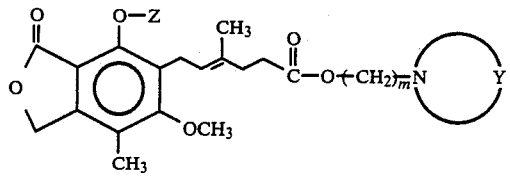

wherein:
m is an integer from two to four;
Z is

in which:
R¹ is cycloalkyl having seven or more carbon atoms, or —NR²R³,
where R² is hydrogen or lower alkyl, and
R³ is hydrogen, lower alkyl, —phenyl—$CO_2R^2$ or a pharmaceutically acceptable cation;
Y is lower alkylene of four to six carbon atoms, or lower alkylene of three to five carbon atoms plus one member that is —O—, —S—, or

where R⁸ is hydrogen or alkyl of one to five carbon atoms; or a pharmaceutically acceptable salt thereof.

2. The compound of claim 1 wherein Y is —CH₂—CH₂—O—CH₂—CH₂—.
3. The compound of claim 1 wherein Z is 1-adamantoyl.
4. The compound of claim 2 wherein Z is 1-adamantoyl.
5. The compound of claim 1 wherein m is 2.
6. The compound of claim 2 wherein m is 2.
7. The compound of claim 3 wherein m is 2.
8. The compound of claim 4 wherein m is 2.
9. A pharmaceutical composition comprising a pharmaceutically acceptable non-toxic excipient and a therapeutically effective amount of a compound of claim 1.

* * * * *